(12) United States Patent
Köhler et al.

(10) Patent No.: US 7,700,805 B2
(45) Date of Patent: Apr. 20, 2010

(54) PROCESS FOR PREPARING AMINES

(75) Inventors: Günther Köhler, Marl (DE); Manfred Neumann, Marl (DE); Marianne Omeis, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/118,884

(22) Filed: May 12, 2008

(65) Prior Publication Data

US 2008/0281126 A1    Nov. 13, 2008

(30) Foreign Application Priority Data

May 10, 2007    (DE) .................. 10 2007 022 445

(51) Int. Cl.
*C07C 209/62*    (2006.01)
(52) U.S. Cl. .................. 564/463; 564/468; 564/470; 564/486
(58) Field of Classification Search .................. None
See application file for complete search history.

(56) References Cited

U.S. PATENT DOCUMENTS

| 5,220,069 | A | 6/1993 | King et al. |
| 2002/0041838 | A1 | 4/2002 | Rizzi |
| 2008/0219900 | A1 | 9/2008 | Romiti et al. |

FOREIGN PATENT DOCUMENTS

| EP | 0 480 493 A2 | 4/1992 |
| EP | 1 195 194 A1 | 4/2002 |
| EP | 1 700 847 A1 | 9/2006 |
| JP | 2001-262892 A | 9/2001 |
| JP | 2006-069941 A | 3/2006 |
| WO | WO 2006/094541 A2 | 9/2006 |

OTHER PUBLICATIONS

U.S. Appl. No. 11/961,109, filed Dec. 20, 2007, Omeis, et al.

Sheila P. Ewing, et al., "Mechanism of Cleavage of Carbamate Anions[1]", Journal of the American Chemical Society, 102:9, Apr. 23, 1980, pp. 3072-3084.
Ulrich Jacquemard, et al., "Mild and Selective Deprotection of Carbamates With $Bu_4NF$", Tetrahedron, vol. 60, Issue 44, Oct. 25, 2004, pp. 10039-10047.
George L. Gaines, Jr., "The Structure of N-(2-Ammonioethyl) Carbamate in Solution", J. Org. Chem., 1985, 50, pp. 410-411.
Jean-Michel Vatèle, "One-Pot Selective Cleavage of Prenyl Carbamates Using Iodine in Methanol Followed by Zinc", Tetrahedron Letters 44 (2003), pp. 9127-9129.

*Primary Examiner*—Brian J Davis
(74) *Attorney, Agent, or Firm*—Oblon, Spivak, McClelland, Maier & Neustadt, L.L.P.

(57) ABSTRACT

An amine is prepared by cleaving a carbamate of the formula I

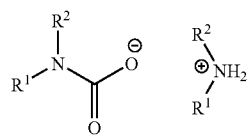

wherein $R^1$=hydrogen, alkyl, aryl or phenyl group, $R^2$=alkyl, aryl or phenyl group, wherein $R^1$ and $R^2$ are independently substituted or unsubstituted, wherein the cleaving of the carbamate is performed in the presence of an acid of the formula II

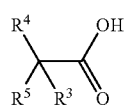

wherein $R^3$, $R^4$ and $R^5$ are independently alkyl or phenyl group, wherein $R^1$, $R^2$, $R^3$, $R^4$ and $R^5$ are the same or different.

20 Claims, No Drawings

PROCESS FOR PREPARING AMINES

BACKGROUND OF THE INVENTION

1. Field of the Invention

The present invention relates to a process for preparing amines by catalytic cleaving of carbamates.

2. Discussion of the Background

The cleaving, i.e. the decarboxylation, of carbamates is a common process for preparing amines. The resulting amines are in turn starting compounds for numerous industrial intermediates and active pharmaceutical ingredients.

The general reaction mechanism of the cleaving of carbamates is described by Ewing et al. in their publication J. Amer. Chem. Soc. (1980) 102(9), 3072-3084:

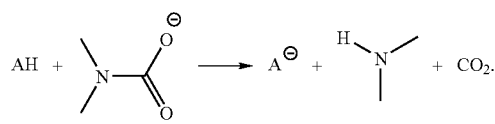

The cleaving of carbamates in the presence of tetra-n-butylammonium fluoride ($Bu_4NF$) is described by Jacquemard et al. in Tetrahedron (2004) 60(44), 10039-10047:

where

R=methyl, ethyl, tert-butyl, benzyl, allyl or phenyl,
R' is alkyl or aryl,
R" is hydrogen, alkyl or aryl.

The general structure of the carbamates is described by Gaines in J. Org. Chem. (1985) 50, 410-411 as a monomolecular zwitterion or disalt.

Japanese publication JP 2006-069941 A describes, inter alia, the thermal decomposition of carbamates to prepare isocyanates. In contrast, JP 2004-262892 A describes the thermal decomposition of carbamates in the presence of a tin catalyst and of a solid catalyst selected from silicates, silica gel and/or metal.

The decomposition of ammonium carbamate to ammonia and carbon dioxide is described by WO 2006/094541 A and EP 1 195 194 A.

The cleaving of carbamates in the presence of a tin catalyst is also described in JP 2004-262892 A. The use of iodine to cleave carbamates is described by Vatele et al. in Tetrahedron Letters (2003), 44(51), 9127-9129.

DETAILED DESCRIPTION OF THE INVENTION

It was an object of the present invention to provide a process for cleaving carbamates, which allows the carbamate to be cleaved at low temperatures with removal of the carbon dioxide. In particular, reformation of the carbamate from the carbon dioxide and desired amine reaction products should be avoided. In particular, it was an object of the invention to develop a continuous preparation process for this purpose.

This and other objects have been achieved by the present invention the first embodiment of which includes a process for preparing an amine by cleaving a carbamate of the formula I

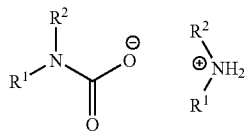

wherein
$R^1$=hydrogen, alkyl, aryl or phenyl group,
$R^2$=alkyl, aryl or phenyl group,
wherein $R^1$ and $R^2$ are independently substituted or unsubstituted,
wherein the cleaving of the carbamate is performed in the presence of an acid of the formula II

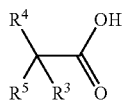

wherein $R^3$, $R^4$ and $R^5$ are independently alkyl or phenyl group,
wherein $R^1$, $R^2$, $R^3$, $R^4$ and $R^5$ are the same or different.

It has been found that, surprisingly, a process for preparing amines by cleaving carbamates in the presence of an acid enables a continuous procedure. The acids used in the process according to the invention are high-boiling neo acids, which surprisingly possess catalytic action in the carbamate cleaving. In addition to the catalytic action, these acids also serve as bottom diluents in the process according to the invention.

It was all the more surprising that it was possible to use the carbamate to be cleaved as a solution or else as a suspension, while being able to remove carbon dioxide and the solvent of the carbamate used from the reaction zone without also removing the amine target product. Owing to the lower reaction temperature which is enabled through the use of the acids, the amine target product remains in the acid which thus serves, as well as a catalyst, also as a solvent for the amine. In this way, the process according to the invention enables the separate removal of the carbon dioxide formed and of the amine target product. The reformation of the carbamate can thus be prevented. This is a crucial advantage over the conventional processes, since the cleaving of the carbamate here proceeds at higher temperatures, such that both the carbon dioxide and the amine target product are transferred to the gas phase and thus reform the carbamate.

It was also not obvious that it would be possible to remove the amine to be isolated from the reaction zone in a simple manner and that it would not react with the acid to form an acid amide. Instead, the amine can be isolated completely and in very high purity from the reaction zone which contains the acid. The process according to the invention can surprisingly be applied to a large number of carbamates, such that it is possible to prepare both aliphatic and aromatic amines in this way. In this way, it is possible to provide a semibatchwise process and, in a specific embodiment, also a continuous process. The process according to the invention also has the advantage that it proceeds without the use of metals and/or or metal compounds.

The invention thus provides a process for preparing amines by cleaving carbamates of the formula I

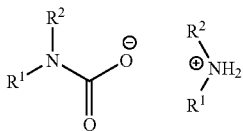

where
R$^1$=hydrogen, alkyl, aryl or phenyl group,
R$^2$=alkyl, aryl or phenyl group,
where the substituents of the R$^1$ and R$^2$ type are substituted or unsubstituted, wherein
the cleaving of the carbamate is performed in the presence of an acid of the formula II

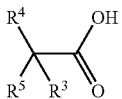

where R$^3$, R$^4$ and R$^5$=alkyl or phenyl group,
where the substituents of the R$^1$, R$^2$, R$^3$, R$^4$ and R$^5$ type are the same or different.

The acids used in the process according to the invention are compounds of the formula II. In the process according to the invention, preference is given to using so-called neo acids or Koch acids. These acids have the advantage that they, owing to the quaternary α-carbon atom, are particularly hydrolysis- and oxidation-stable. Preference is given to using acids of the formula II which have an alkyl group as substituents of the R$^3$, R$^4$ and R$^5$ type, especially acids of the formula II having a methyl group as the substituent of the R$^4$ and R$^5$ type and, as the substituent of the R$^3$ type, a group of the formula III

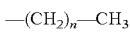  —(CH$_2$)$_n$—CH$_3$    III where n=0-8, preferably n=2-7.

In the process according to the invention, particular preference is given to using high-boiling neo acids, especially having a total number of carbon or 5 to 12. Very particular preference is given to using neodecanoic acid (R$^4$ and R$^5$=methyl, R$^3$=—(CH$_2$)$_5$—CH$_3$) as the acid. In the process according to the invention, it is also possible to use mixtures of these acids of the formula II, in which case these mixtures of acids may also comprise isomers of the acids of the formula II.

It is advantageous to use acids which have a boiling point of at least 150° C. at a pressure of 1013 mbar. The acids used in the process according to the invention preferably have a boiling point of 160 to 300° C. The boiling point includes all values and subvalues therebetween, especially including 170, 180, 200, 210, 220, 230, 240, 250, 260, 270, 280 and 290° C.

The acids used in the process according to the invention are notable for their high boiling point, but also for their acid-catalytic activity in the cleaving of carbamates.

In the process according to the invention, carbamates of the formula I are cleaved to the corresponding amines. Preference is given to using carbamates of the formula I where R$^1$=hydrogen and R$^2$=alkyl group, but particular preference is given to using carbamates of the formula I where R$^1$=hydrogen and R$^2$=—(CH$_2$)$_n$—CH$_3$ where n=0-8, preferably n=2-7, in the process according to the invention. In a particular embodiment of the process according to the invention, carbamates of the formula I where R$^1$=hydrogen and R$^2$=alkyl group, where the alkyl group is substituted, are used. In particular, carbamates of the formula I where R$^1$=hydrogen and R$^2$=alkyl group which is substituted by amino groups, preferably one amino group, are suitable for this process. Preference is thus given to using carbamates of the formula I where R$^1$=hydrogen and R$^2$=—(CH$_2$)$_n$—NH$_2$ where n=1-8, especially 2-7.

In the process according to the invention, the carbamate to be cleaved can be used as a solution, suspension or as a solvent-comprising solid. In the process according to the invention, preference is given to using solvents which have a boiling point of 30 to 300° C., more preferably of 50 to 150° C. The boiling point includes all values and subvalues therebetween, especially including 40, 50, 60, 70, 80, 90, 100, 110, 120, 130, 140, 150, 160, 170, 180, 190, 200, 210, 220, 230, 240, 250, 260, 270, 280 and 290° C.

In the process according to the invention, the solvents used for the carbamates may be alcohols, for example methanol, ethanol, isopropanol or cyclohexanol, aliphatic hydrocarbons, for example hexane, heptane, octane, nonane or decane, cycloaliphatic hydrocarbons, for example cyclohexane or aromatic hydrocarbons, for example toluene or xylene. The concentration of carbamate in the carbamate solution or else carbamate suspension used is preferably 5 to 80% by weight, preferably from 10 to 50% by weight. The concentration of carbamate includes all values and subvalues therebetween, especially including 10, 20, 30, 40, 50, 60 and 70% by weight.

It is advantageous in the process according to the invention to initially charge the acid in the reaction zone at the desired reaction temperature and only then to supply the carbamate to the reaction zone.

Preference is given to using 0.1 to 1000 molar eq., preferably 0.5 to 500 molar eq., of acid in the process according to the invention, based on the amount of carbamate used. The amount of acid includes all values and subvalues therebetween, especially including 0.5, 1, 5, 10, 50, 100, 200, 300, 400, 500, 600, 700, 800 and 900 molar eq., based on the amount of carbamate used.

As a result of the use of acids of the formula II, a correspondingly high reaction temperature is possible in the metered addition of the carbamate during the cleaving in the process according to the invention, the reaction temperature being sufficiently high for the cleaving of the carbamate but also sufficiently low that transfer of the amine target product to the gas and/or vapour phase can be suppressed. In this way, the solvent which is introduced into the reaction zone through the addition of carbamate can be removed again rapidly from the reaction zone. The cleaving of the carbamate in the process according to the invention is performed preferably at a reaction temperature of 50° C. to 320° C., preferably of 120° C. to 250° C. The reaction temperature includes all values and subvalues therebetween, especially including 60, 70, 80, 90, 100, 110, 120, 130, 140, 150, 160, 170, 180, 190, 200, 210, 220, 230, 240, 250, 260, 270, 280, 290, 300 and 310° C. The reaction temperature is preferably selected such that no amine target product can also be distilled over or be entrained with the removal of the carbon dioxide. In general, an advantageous reaction temperature in the bottom is one which is 20 to 30 K below the boiling point of the amine.

The pressure at which the cleaving of the carbamate in the process according to the invention is performed is preferably 20 mbar to 2000 mbar, preferentially 800 to 1200 mbar and more preferably 950 to 1100 mbar. The pressure includes all values and subvalues therebetween, especially including 50, 100, 200, 300, 400, 500, 600, 700, 800, 900, 1000, 1100, 1200, 1300, 1400, 1500, 1600, 1700, 1800 and 1900 mbar.

Very particular preference is given to performing the cleaving of the carbamate in the process according to the invention at atmospheric pressure.

The process according to the invention can be operated either as a batchwise process or as a continuous process, but is preferably operated as a continuous process.

In a preferred embodiment of the process according to the invention, continuous delay reactors, for example tubular reactors, falling-film or trickle-film evaporators, thin-layer evaporators or thin-film extruders, are used. In these reactor types, in the process according to the invention, the acid of the formula II is preferably circulated and the carbamate to be cleaved—for example in the form of a solution or suspension—is fed to the reaction zone in this apparatus. It is also possible not to circulate the acid and thus to feed the acid back to the reactor only after a separate workup or to discard it.

The cleaving forms carbon dioxide which can thus be removed continuously from the reaction zone together with the solvent introduced into the reaction zone—for example water. Owing to the high evolution of $CO_2$ during the cleaving of the carbamate, it is advantageous to provide a large evaporator surface area; falling-film, trickle-film or thin-layer evaporators are therefore particularly suitable for the process according to the invention.

In order that the amine obtained after the cleaving of the carbamate does not come into contact with the carbon dioxide which likewise forms, thus resulting in a back-reaction to give the carbamate, the carbon dioxide formed is stripped out by an inert gas stream, for example nitrogen.

After the cleaving of the carbamate, the amine obtained from the cleaving can be drawn off in the process according to the invention. This is achieved, for example, by a distillative route by a further increase in the temperature and/or lowering of the pressure, which removes the amine from the reaction zone.

The remaining bottom phase comprising the acid of the formula II may, in the process according to the invention, subsequently be provided again to a cleaving of carbamates, by virtue of a downstream repeated circulation or, in the simplest case, a further downstream semibatchwise cycle, for example in a stirred tank reactor.

The amine obtained in the process according to the invention generally has a sufficiently high purity that no further purification steps are required. In particular, it is possible by means of the process according to the invention to obtain amines having a GC purity of >98 area %. The purity includes all values and subvalues therebetween, especially including 98.5, 99, 99.5, 99.8, 99.9, 100 area %. Should the amine, however, not be in the desired purity, a further distillation or rectification may follow.

It is advantageous to work under inert gas in all workup steps in the process according to the invention in order to prevent the reformation of carbamates which can reform from the amine reaction product and $CO_2$ from the atmosphere.

The examples which follow are intended to illustrate the process according to the invention for preparing amines in detail without any intention that the invention be restricted to this embodiment.

EXAMPLES

Example 1

According to Invention

A 1 l flask with a stirrer and a 10 cm column with random packing, a column head and a condenser was initially charged with 200 g of neodecanoic acid (Versatic 10 from Resolution). This liquid phase was heated to approx. 120° C. Within 2 hours, 800 g of a 30% by weight aqueous solution of a carbamate of the formula I where $R^1$=H and $R^2$=—$(CH_2)_6$—$NH_2$ (this corresponds to 0.87 mol of carbamate) were metered in. Within these 2 hours, approx. 550 g of water were removed by distillation and approx. 19 l of carbon dioxide were released. The determination of the carbon dioxide formed was monitored with a suitable gas meter. Once the carbon dioxide formation had ended and all of the water had been removed, the pressure was reduced to such an extent that the residual water can also be removed. With further reduction of the pressure, 1,6-diaminohexane was then distilled off.

Approx. 95 g of 99% 1,6-diaminohexane were obtained; this corresponds to a yield of approx. 95%.

Comparative Example 1

Comparative Example 1 was performed under conditions analogous to those in Example 1, except that 200 g of Marlotherm SH were used instead of 200 g of neodecanoic acid. No thermal cleaving of the carbamate was observed. Merely distillative removal of the water was observed. The uncleaved carbamate remained in the liquid phase.

Comparative Example 2

Comparative Example 2 was performed under conditions analogous to those in Comparative Example 1, except that the bottom temperature was heated to 200° C. Now, thermal carbamate cleaving was observed, but the amine and carbon dioxide formed were present simultaneously in the vapour space of the reactor, such that a back-reaction of the carbamate was observed.

In Comparative Examples 1 and 2, no amine was isolated.

Example 2

According to Invention

A glass thin-film evaporator with a surface area of 0.1 m² was charged with approx. 500 g/h of neodecanoic acid with the aid of a metering pump. The heat carrier feed temperature at the thin-film evaporator was approx. 180° C. With the aid of a second metering pump, the thin-film evaporator was charged with approx. 200 g/h of a 30% by weight aqueous solution of a carbamate of the formula I where $R^1$=H and $R^2$=—$(CH_2)_6$—$NH_2$. Approx. 120 g/h of water were distilled off via the top. At the same time, as a result of the $CO_2$ elimination, it was possible to monitor gas evolution with the aid of a customary gas volume meter (approx. 4-5 l/h of carbon dioxide were formed). Neodecanoic acid and 1,6-diaminohexane remain in the bottom of the thin-film evaporator, which can subsequently be separated from one another by distillation either on a further thin-film evaporator or by simple short-path distillation.

The two process variants in Example 2 led to a yield of 1,6-diaminohexane based on the carbamate used of approx. 95%.

German patent application 10 2007 022445.3 filed May 10, 2007, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing an amine, comprising:
cleaving a carbamate of the formula I

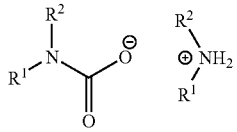

wherein
$R^1$=hydrogen, alkyl, aryl or phenyl group,
$R^2$=alkyl, aryl or phenyl group,
wherein $R^1$ and $R^2$ are independently substituted or unsubstituted,
wherein the cleaving of the carbamate is performed in the presence of an acid of the formula II

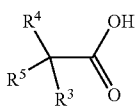

wherein $R^3$, $R^4$ and $R^5$ are independently alkyl or phenyl group,
wherein $R^1$, $R^2$, $R^3$, $R^4$ and $R^5$ are the same or different.

2. The process as claimed in claim 1, wherein, in the acid of the formula II, $R^4$ and $R^5$ are each a methyl group and $R^3$ is a group of the formula III

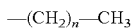

—(CH$_2$)$_n$—CH$_3$    III wherein n=0-8.

3. The process as claimed in claim 1, wherein the acid used is neodecanoic acid.

4. The process as claimed in claim 1, wherein the carbamate is used as a solution, or as a solid which comprises a solvent.

5. The process as claimed in claim 4, wherein the solvent of said solution, or said solid comprising a solvent has a boiling point of 30° C. to 300° C.

6. The process as claimed in claim 1, wherein the acid is initially charged in a reaction zone at a desired reaction temperature and only then is the carbamate supplied to the reaction zone.

7. The process as claimed in claim 1, wherein 0.1 to 1000 molar eq. of acid is used, based on a total amount of the carbamate.

8. The process as claimed in claim 1, wherein the cleaving of the carbamate is performed at a reaction temperature of 50° C. to 320° C.

9. The process as claimed in claim 1, wherein the carbamate to be cleaved is used as a solution or as a suspension, wherein carbon dioxide and the solvent of the carbamate are removed from a reaction zone without removing the amine.

10. The process as claimed in claim 1, wherein said amine remains in the acid which serves as a catalyst and as a solvent for the amine.

11. The process as claimed in claim 1, comprising separately removing carbon dioxide formed and the amine.

12. A process for preparing an amine, comprising:
cleaving a carbamate of the formula I

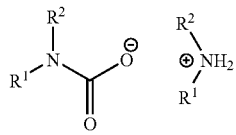

wherein
$R^1$=hydrogen, alkyl, aryl or phenyl group,
$R^2$=alkyl, aryl or phenyl group,
wherein $R^1$ and $R^2$ are independently substituted or unsubstituted,
wherein the cleaving of the carbamate is performed in the presence of an acid of the formula II

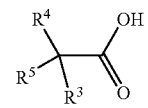

wherein $R^3$, $R^4$ and $R^5$ are independently alkyl or phenyl group,
wherein $R^1$, $R^2$, $R^3$, $R^4$ and $R^5$ are the same or different,
thereby preventing the reformation of the carbamate.

13. A process for preparing an amine, comprising
cleaving a carbamate of the formula I

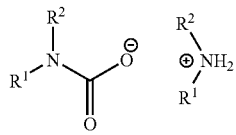

wherein
$R^1$=hydrogen, alkyl, aryl or phenyl group,
$R^2$=alkyl, aryl or phenyl group,
wherein $R^1$ and $R^2$ are independently substituted or unsubstituted,
wherein the cleaving of the carbamate is performed in the presence of an acid of the formula II

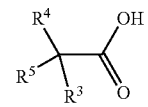

wherein $R^3$, $R^4$ and $R^5$ are independently alkyl or phenyl group,
wherein $R^1$, $R^2$, $R^3$, $R^4$ and $R^5$ are the same or different,
wherein the amine to be isolated from a reaction zone does not react with the acid to form an acid amide.

14. The process as claimed in claim 1, wherein said amine is aliphatic or aromatic.

15. The process as claimed in claim 1, which proceeds without the use of metals and/or or metal compounds.

16. The process as claimed in claim 1, wherein a mixture of acids of formula II is used.

17. The process as claimed in claim 1, wherein said acid has a boiling point of at least 150° C. at a pressure of 1013 mbar.

18. The process as claimed in claim 1, wherein, in said carbamate of the formula I, $R^1$=hydrogen and $R^2$=alkyl group which is substituted.

19. The process as claimed in claim 1, wherein, in said carbamate of the formula I, $R^1$=hydrogen and $R^2$=—$(CH_2)_n$—$NH_2$ wherein n=1-8.

20. A process for preparing an amine by cleaving a carbamate of the formula I

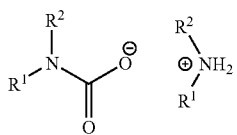

wherein
$R^1$=hydrogen, alkyl, aryl or phenyl group,
$R^2$=alkyl, aryl or phenyl group,
wherein $R^1$ and $R^2$ are independently substituted or unsubstituted,
wherein the cleaving of the carbamate is performed in the presence of an acid of the formula II

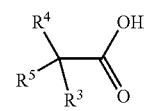

wherein $R^3$, $R^4$ and $R^5$ are independently alkyl or phenyl group,
wherein $R^1$, $R^2$, $R^3$, $R^4$ and $R^5$ are the same or different.

* * * * *